United States Patent [19]

Taylor et al.

[11] Patent Number: 5,081,289
[45] Date of Patent: Jan. 14, 1992

[54] SYNTHESIS AND ISOLATION OF NOPALINE AND ITS ANALOGUES

[75] Inventors: Kenneth B. Taylor, Birmingham; Leo M. Hall, Homewood, both of Ala.

[73] Assignee: The University of Alabama in Birmingham, Birmingham, Ala.

[21] Appl. No.: 358,492

[22] Filed: May 30, 1989

Related U.S. Application Data

[63] Continuation of Ser. No. 75,221, Jul. 20, 1987, abandoned, which is a continuation of Ser. No. 523,081, Aug. 15, 1983, abandoned.

[51] Int. Cl.⁵ .................. C07C 241/00; C07B 55/00
[52] U.S. Cl. ............................ 562/401; 548/534; 562/560; 435/252.2
[58] Field of Search ....................... 562/401, 560

[56] References Cited

PUBLICATIONS

Cooper, Org. Prep. Proced. Int., 9(2) pp. 99–101 (1977).
Hatanaka, Phytochemistry, 21, pp. 225–227 (1982).
Hall, J. Biol. Chem., 258, pp. 7276–7279 (Received in PTO 6/28/83).
Jensen, Biochem. Biophys. Res. Commun., 75, pp. 1066–1070 (1977).

*Primary Examiner*—Michael L. Shippen
*Attorney, Agent, or Firm*—Oblon, Spivak, McClelland, Maier & Neustadt

[57] ABSTRACT

A method of separating nonpaline derivatives from their diastereoisomers is disclosed along with a method of selectively growing strains of the bacterium *A. tumefaciens*. Also disclosed are novel general methods of synthesizing the nopaline and isonopaline of this invention. These novel compounds are useful for the selective growth of the agriculturally useful *A. tumefaciens* bacterium.

5 Claims, 1 Drawing Sheet

SYNTHESIS AND ISOLATION OF NOPALINE AND ITS ANALOGUES

This application is a Continuation of application Ser. No. 07/075,221, filed on July 20, 1987, now abandoned, which is a Continuation of application Ser. No. 06/523,081, filed Aug. 15, 1983, now abandoned.

BACKGROUND OF THE INVENTION

1. Field of the Invention

The present invention relates to a method for the isolation of nopaline and its analogues from diastereomers of these compounds.

2. Description of the Prior Art

Considerable activity exist in the area of genetic engineering of microorganisms. However, only recently has there been significant activity involving genetic engineering of higher plants. One method which has been proposed for introducing genetic material into higher plants involves use of the bacterium *Agrobacterium tumefaciens* to induce a crown gall tumor in a dicotyledoneous plant. Variant *A. tumefaciens* bacterial strains contain a large Ti (tumor-inciting) plasmid, part of which, a specific segment called the T-DNA (transferred DNA), integrates into the plant nuclear DNA where it is retained and expressed even after the tumors redifferentiate. Accordingly, the Ti plasmid is a possible vector for accomplishing genetic engineering in plants. See, *Ream and Gordon*, "Crown Gall Disease and Prospects for Genetic Manipulation of Plants", Science, 218: 854–859 (1982).

Crown gall tumor cells produce opines, which are unusual amino acid derivatives not found in normal plant cells. The ability of transformed cells to synthesize these amino acid derivatives depends strictly on the bacterial strain Which causes the tumor. Furthermore, bacteria which induce a specific amino acid derivative can utilize that derivative as a single source of carbon and nitrogen, but cannot utilize opines produced by tumors caused by other strains of bacteria. Accordingly, opines can be utilized in the preparation of bacterial growth media useful for the selection of appropriate strains of bacteria. Other derivatives are toxic to the bacteria containing the appropriate catabolic enzymes coded in the Ti plasmid. See *Petit and Tempe*, "Isolation of Agrobacterium Ti-plasmid Regulatory Mutants", Molec. Gen. Genet. 167:147–155 (1978). Use of these derivatives in selective media permits selection of mutant strains of bacteria which do not have the ability to catabolize the toxic derivatives.

Accordingly, a source of opines useful for producing the selective media is needed. While it is possible to isolate different opines from crown gall tumors of plants, the isolation techniques are tedious and a general synthetic method capable of synthesizing different opines in good yield is needed. See *Fermin and Fenwick*, Phytochemistry 16:761–762 (1977).

Synthetic procedures for the synthesis of opines and particularly for the synthesis of nopaline and its derivatives exist in the prior art but suffer from disadvantages caused by the difficulty of separating nopaline (or an analog of nopaline) from the diastereoisomer produced by the synthetic method, known as isonopaline (or the corresponding isonopaline analogue).

Cooper and Firmin, *Org. Prep. Proced. Int.*, 9: 99–101 (1977) disclose a chemical synthesis of nopaline and isonopaline by the base catalyzed condensation of 2-oxoglutaric acid with L-arginine, followed by borohydride reduction of the resulting Schiff's base. The product was dissolved in boiling water and a precipitate was obtained uponstanding at 4° C. However, because of the heating step, although unknown at the time, this product was not pure nopaline. The thus obtained precipitate was substantially contaminated at least with the cyclized derivative, or pyronopaline. In the same fashion, the precipitate obtained from the mother liquor by addition of ethanol, was not pure isonopaline, but contained at least some amount of the cyclized derivative, or pyroisonopaline.

Jensen et al, Biochemical and Biophysical Research Communications, 75: 1066–1070 (1977), disclose a similar reaction for synthesizing the nopaline diastereoisomers but using cyanoborohydride instead of borohydride which gave a 80% yield, substantially higher than that obtained with sodium borohydride. A weakly levorotatory nopaline was obtained in a 2–4% yield, which is presumed by the investigators to be a diostereoisomeric mixture of the weakly levorotatory natural nopaline and of the strongly dextrorotatory isonopaline having the L- configuration at both centers (see, reference, page 1069, last paragraph). However, as shown in the present application, both nopaline and isonopaline are strongly dextrorotatory when in substantially purified form. Thus, both the natural and synthetic nopaline of Jensen et al are substantially contaminated.

Hatanaka et al, Phytochemistry 21(1):225–227 (1981) disclose a variation of the cyanoborohydride reaction which gave a total yield of nopaline and isonopaline of 70%. In this method the separation of the diastereoisomers was accomplisned by chromatography on an anion exchange substrate.

However, the published analytical data of the results of all these separations indicate that purified nopaline substantially free of isonopaline was not obtained.

Firmin and Fenwick disclose a chemical synthesis of nopalinic acid by the aqueous hydrazinolysis of nopaline, followed by anion exchange chromatography. However, the product was obtained upon recrystallization from aqueous ethanol in a yield of only 42%.

Accordingly, an improved method for the separation of nopaline and its analogs from their diastereoisomers is necessary in order for these synthetic methods to be fully developed.

SUMMARY OF THE INVENTION

Accordingly, it is an object of the present invention to provide a method of separating nopaline or a derivative of nopaline from its diastereoisomer which provides nopaline or the derivative in pure form.

It is still another object of the present invention to provide a general method of synthesizing nopaline or a derivative of nopaline, comprising separating the resulting compounds from their diastereoisomers, thereby providing nopaline or a derivative of nopaline in pure form.

It is still another object of the present invention to provide a method of synthesizing pyronopaline or a derivative of pyronopaline from nopaline or the corresponding derivative of nopaline.

A further object of the present invention is to provide a method of synthesizing nopalinic acid or a nopalinic acid derivative from nopaline or the corresponding nopaline derivative.

Still another object of the present invention is to provide novel nopaline derivatives.

A further object it to provide growth media comprising novel nopaline derivatives.

Another object is to provide a method of selectively growing strains of the bacterium *A. tumefaciens.*

And still a further object is to provide a method of selectively growing cells carrying the Ti plasmid or sequences derived from the plasmid. Another object is to provide a method of selectively growing crown gall tumor cells.

These and other objects of the invention, as will hereinafter become more readily apparent, have been accomplished by providing a method of separating a compound of the formula:

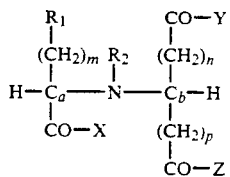

wherein m is 1-4, n is 0-3, p is 0-3,

X, Y and Z are the same or different and represent OH or $NH_2$, with the proviso that at least one of X, Y, and Z is OH, $C_a$ and $C_b$ can be the same or different, and represent the R and S carbon configurations, $R_1$ is $-NHC(NH)NH_2$, $-NH_2$, $-ONH_2$, $-ONHCONH_2$, or $-ONHC(NH)NH_2$, $R_2$ is H, and if n or p are different from zero, $R_2$ and Y may be a cyclic structure containing one carbon ring, from its diastereoisomer, which comprises:

adjusting the pH of an aqueous solution containing said compound and its diastereoisomer to the approximate isoelectric point of the compound, whereby a pH-adjusted solution is obtained;

allowing said pH-adjusted solution to stand until a partially purified first precipitate forms and a mother liquor remains; and collecting said precipitate.

A general method of synthesizing nopaline or a derivative of nopaline is also part of the present invention. This process comprises:

(a) reacting a compound of the formula:

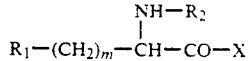

with a compound of the formula:

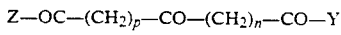

in the presence of cyanoborohydride, (b) separating from the reacting compounds, and then drying, the mixture of diastereoisomers obtained in step (a), (c) dissolving the mixture of diastereoisomers in water, and (d) separating nopaline or the nopaline derivative from its diastereoisomer by using the method hereinbefore described.

The objects of this invention have also been attained by providing a method of synthesizing pyronopaline or a derivative of pyronopaline, comprising:

(a) suspending a nopaline derivative in water, (b) heating the suspension thereby obtaining a cyclic nopaline derivative, and (c) crystallizing the cyclic nopaline derivative.

The objects of the present invention have also been attained by providing a method of synthesizing nopalinic acid or a derivative of nopalinic acid, comprising:

(a) heating a nopaline derivative in the presence of an alkali metal hydroxide at an elevated temperature until the generation of ammonia from the aqueous solution is completed, (b) adjusting the pH of the aqueous solution to the isoelectric point of the compound, and (c) crystallizing the nopalinic acid derivative.

Other objects of the present invention are attained by providing novel nopaline derivatives, e.g., isonopalinic acid, pyronopaline and pyroisonopaline, carboxyoctopine which is a derivative of oxaloacetic acid and arginine and a heretofore unknown derivative of dicarboxyacetone and arginine.

Still another object has been attained by providing bacterial growth media comprising the novel compounds of this invention.

Further, the objects of the invention have also been attained by providing a method of selectively growing strains of the bacterium *A. tumefaciens*, by using media comprising the novel nopaline derivatives of this invention.

The objects have also been attained by providing a method of selectively growing cells carrying the Tiplasmid or sequences derived from the plasmid, by using media comprising the novel nopaline derivatives of the present invention.

A method of selectively growing crown gall tumor cells by using media comprising the novel nopaline derivatives of this invention is hereby also provided.

Other objects, advantages and features of the present invention will become apparent to those skilled in the art from the following discussion.

DESCRIPTION OF THE PREFERRED EMBODIMENTS

Figure 1:
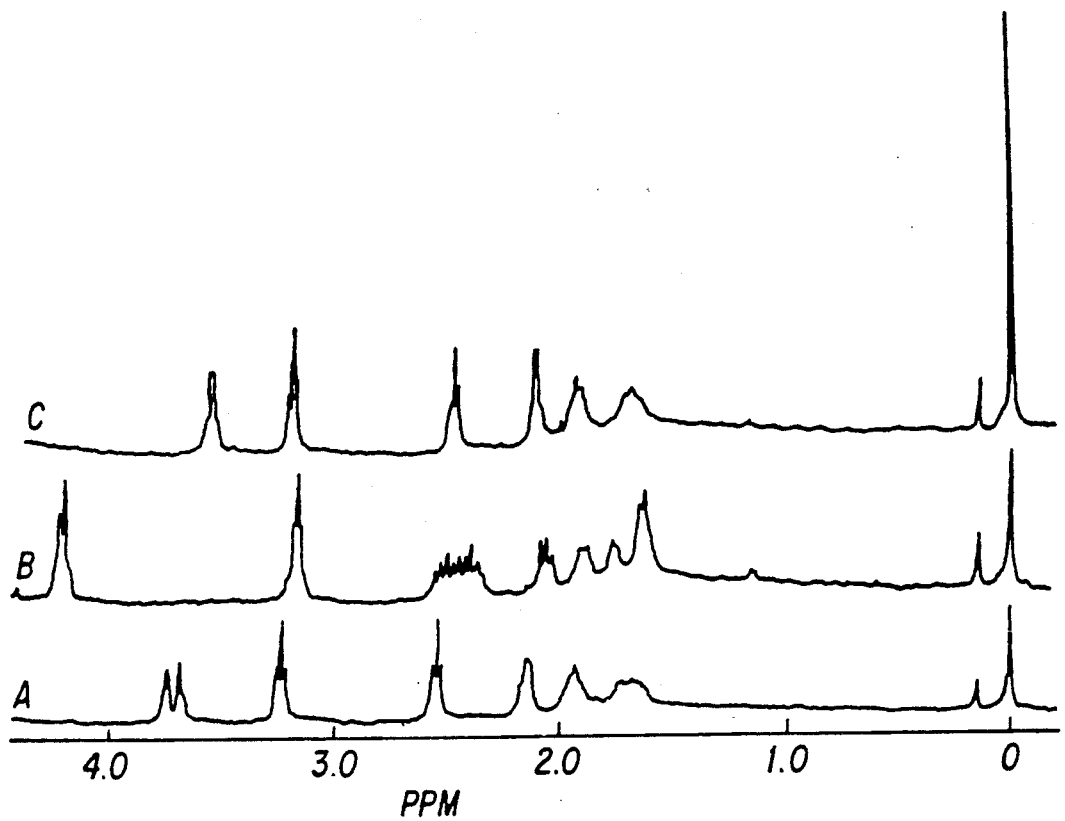
FIG. 1 shows the proton MNR Spectra of nopaline and related compounds. The spectra of nopaline (A), pyronopaline (B), and isonopaline (C) were recorded as described in the Examples.

The present invention provides an improved method of separating nopaline or a derivative of nopaline from its diastereoisomer which provides nopaline and/or the derivative in substantially purified form. The given process provides an improvement over the previously described methods for the crystallization of nopaline and its diastereoisomer. Prior methods resulted in a product wherein nopaline was somewhat contaminated with isonopaline (Jensen et al and Hatanaka et al) or with pyronopaline and pyroisonopaline (Cooper and Firmin) which although unknown to the authors at the time, are formed readily by heating nopaline and isonopaline, respectively.

The method of separating nopaline or a nopaline derivative from its diastereoisomer comprises separating a compound of the formula:

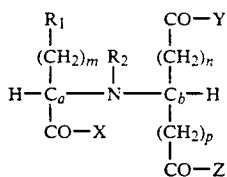

wherein m is 1-4, n is 0-3, p is 0-3,

X, Y and Z are the same or different and represent OH or $NH_2$, with the proviso that at least one of X, Y, and Z is OH, $C_a$ and $C_b$ can be the same or different, and represent the R and S carbon configurations, $R_1$ is $-NHC(NH)NH_2$, $-NH_2$, $-ONH_2$, $-ONHCONH_2$, $-ONHC(NH)NH_2$, or $-NH-CO-NH_2$, $R_2$ is H, and if n or p are different from zero, $R_2$ and Y may be a cyclic structure containing one carbon ring, from its diastereoisomer, which comprises:

adjusting the pH of a first aqueous solution containing said compound and its diastereoisomer to the approximate isoelectric point of the compound, whereby a pH-adjusted solution is obtained;

allowing said pH-adjusted solution to stand until a partially purified first precipitate forms and a mother liquor remains; and collecting said precipitate.

In a preferred embodiment of this method, the starting aqueous solution contains from 0.01 to 1 g/ml of said compound and its diastereoisomer, the pH of the first solution is adjusted to between about 1 and 9 and the pH-adjusted solution is allowed to stand at between about 0° to 40° C. until a precipitate develops.

Other preferred conditions are those where the compound and its diastereoisomer are dissolved in water at between about 0.02 to 0.5 g per ml, the pH of the solution is adjusted to between about 2 and 7, the pH-adjusted solution is allowed to stand at between about 0° to 30° C. until a first precipitate forms and the precipitate is collected by filtration. Still preferred conditions are those where the compounds are dissolved at about 0.05 to 0.15 g/ml, the pH of the first solution is adjusted to about 3.0 to 3.6 and the pH-adjusted solution is allowed to stand at about 0° to 10° C.

The partially purified first precipitate of nopaline or the derivative of nopaline is obtained by this method with a purity of approximately 98% as determined by chromatography or HPLC.

This method may further comprise the following steps:

resuspending said first precipitate in water, thereby obtaining a suspension;

adjusting the pH of said suspension until the precipitate dissolves whereby a second solution is obtained;

adjusting the pH of said second solution to the approximate isoelectric point of the compound, whereby a pH-adjusted second solution is obtained;

allowing said pH-adjusted second solution to stand until a purified first precipitate forms; and collecting said precipitate.

Among the preferred embodiments of this method are those wherein the partially purified first precipitate is resuspended in water at a concentration of between about 0.001 to 1 g per ml and a temperature of between about 0° C. and 40° C., then adjusting the pH of the suspension to between about 3 and 9, adjusting the pH of the second solution to between about 2 and 8 and allowing the pH-adjusted second solution to stand at between about 0° to 40° C. until a purified second precipitate develops.

Other preferred conditions are those wherein the partially purified first precipitate is resuspended in water at a concentration of between about 0.02 and 0.5 g per ml at between about 10° to 30° C. In this case, the pH of the suspension of the first precipitate is adjusted to between about 3.5 to 8.5 to dissolve the precipitate, then adjusting the pH of the second solution to between about 2 to 7 and standing the solution at between about 0° to 20° C. Further preferred conditions are resuspending the partially purified first precipitate at about 0.05 and 0.15 g/ml at between about 15° to 25° C. The pH of the suspension is then adjusted to about 4.5 to 7.5 to dissolve the precipitate, the pH of the solution is then adjusted to 3.0 to 3.6 and the pH-adjusted solution is allowed to stand at 0° to 10° C.

In another embodiment of the present invention, the method of separating a nopaline or a derivative of nopaline from its diastereoisomer may further comprise:

adding to the mother liquor a water miscible organic solvent having a dielectric constant lower than that of water, until a partially purified second precipitate forms; and collecting said partially purified second precipitate.

In yet another embodiment of the present invention, the method further comprises:

dissolving said partially purified second precipitate in a minimum amount of water, whereby a solution of said partially purified second precipitate is obtained;

adding to the solution of the partially purified second precipitate a water miscible organic solvent having a dielectric constant lower than that or water, until a purified second precipitate forms; and collecting said purified second precipitate.

Some of the preferred conditions for this method are those wherein the water miscible organic solvent represents ethanol or acetone and the volume of solvent added is between about 1 to 10 times the volume of water, the solvent mixture is allowed to stand at between about $-40°$ to 40° C.

Other preferred conditions are adding about 1.5 to volumes of the organic solvent per volume of solution and allowing the solvent mixture to stand at about $-10°$ to 20° C. The most preferred conditions are adding about 2 to 5 volumes of solvent, preferably 3 volumes, per volume of solution and allowing the solvent mixture to stand at about 0° to 10° C. The precipitate may be collected by filtration.

In addition, preferred conditions for the recrystallization of the isonopaline or isonoapline derivative are those wherein the partially purified second precipitate is dissolved at 0.01 to 1 g/ml and about 0° and 40° C., then 1 to 10 volumes of the organic solvent are added per volume of solution and the solvent mixture is allowed to stand at about $-40°$ to 40° C. Other preferred conditions are dissolving the partially purified second precipitate at 0.02 to 0.5 g/ml and about 10° to 30° C., then adding 1.5 to 7 volumes of an organic solvent and allowing the solvent mixture to stand at about $-10°$ to 20° C. The most preferred conditions are adding about 2 to 5 volumes of solvent, preferably 3 volumes, per volume of aqueous solution, and allowing the solvent mixture to stand at about 0 to 10° C. The purified precipitate may be collected by filtration.

Typically, the purified diastereoisomer compounds which are obtained by these methods have a purity of approximately 98% for the partially purified second precipitate or greater than 99% for the purified second precipitate as determined by electrophoresis or HPLC.

The present invention also provides a method of synthesizing nopaline or a derivative of nopaline and its diastereoisomer, comprising:

reacting a compound of the formula:

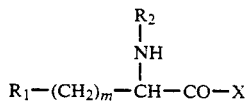

with a compound of the formula:

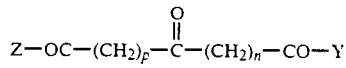

in the presence of cyanoborohydride at a neutral pH thereby obtaining a first solution of a crude mixture of nopaline or a nopaline derivative and its diastereoisomer;

separating the nopaline or nopaline derivative and its diastereoisomer from the reacting compounds, thereby obtaining a diastereoisomer mixture; and separating the nopaline or nopaline derivative from its diastereoisomer in the partially purified first mixture by using the methods hereinbefore described.

One of the preferred embodiments of the present method is that wherein the nopaline or nopaline derivative is separated from the reacting compounds by:

adjusting the pH of the first solution with the crude mixture of nopaline or the nopaline derivative and its diastereoisomer to below about 3 thereby allowing the release of HCN and obtaining a pH-adjusted crude solution;

subjecting the pH-adjusted crude solution to cationic chromatography, thereby obtaining a diastereoisomer mixture;

drying the diastereoisomer mixture thereby obtaining a solid diastereoisomer mixture; and dissolving the diastereoisomer mixture in a minimum amount of water, thereby obtaining a solution of nopaline or a nopaline derivative and its diastereoisomer.

Preferred conditions for the cyanoborohydride reaction are a pH of between 6 and 8 and a temperature between 0° and 40° C., preferably at about 10° to 30° C., and most preferably 15° to 25° C. Also preferred conditions for this method are those wherein the pH of the solution containing the crude diastereoisomer mixture is adjusted after the reaction is completed to below about 2 to permit the release of HCN. The pH-adjusted crude solution is then chromatographed on a strong cationic substrate, washed with water and the diastereoisomer mixture is eluted with aqueous ammonia and dried until a powdery material is obtained. This solid diastereoisomer mixture is dissolved in water at a concentration of between about 0.01 and 1 mg per ml, preferably 0.02–0.5 g/ml and the nopaline or nopaline derivative is separated from its diastereoisomer by the methods already described. More preferred conditions are those wherein after the reaction is completed the pH of the crude solution is adjusted to below about 1, the chromatographed diastereoisomer mixture is dried, preferably in vacuo or by lyophilization; and the solid diastereoisomer mixture is dissolved in water at an approximate concentration of 0.05 to 0.15 g per ml, preferably at 0.1 g/ml.

A method of synthesizing pyronopaline (or pyroisonopaline) or a derivative of pyronopaline (or pyroisonopaline) from nopaline (or isonopaline) or the corresponding derivative of nopaline (or isonopaline) is also hereby provided. This method comprises: suspending in water a compound of the formula:

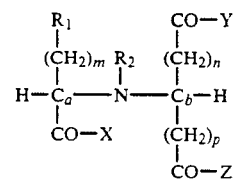

wherein n or p are different from zero, and $R_1$, $R_2$, X, Y, Z, n, m and p are as previously defined, thereby obtaining a suspension of the compound;

heating said suspension whereby a solution containing a pyro-derivative is obtained;

adjusting the pH of said pyro-derivative solution to the approximate isoelectric point of the compound, whereby a pH-adjusted solution is obtained;

adding to the pH-adjusted solution a water-miscible organic solvent having a dielectric constant lower than that of water, until a partially purified precipitate forms; and collecting said precipitate.

Preferred conditions for the reaction are those comprising suspending the compounds in water at a concentration of between about 0.001 to 1 g per ml, adjusting the pH of the solution to between about 0 to 5 or heating at between about 40°–200° C.

Another group of preferred conditions for this synthetic method comprise suspending the nopaline or nopaline derivative in water at a concentration of between about 0.01 to 0.5 g/ml at a pH of between about 0.0 and 3.6, and heating the suspension at between about 60°–130° C. or until the formation of the pyro-derivative is substantially quantitative.

One of the most preferred conditions are those comprising suspending nopaline or isonopaline in water at approximately about 0.05–0.35 g per ml at a pH of about 3.2 to 3.4 or the pH established by the compounds themselves and heating the nopaline or nopaline derivative (isonopaline or isonopaline derivative) solution at 80°–110° C. to obtain the pyro-derivative.

Typical reaction times are between about 30 minutes to 200 hours.

Preferred conditions for the crystallization of pyronopaline or a pyronopaline derivative or its diastereoisomer are adjusting the pH of the solution to about 1 to 9, preferably 2 to 7, and most preferably 3 to 3.6, and adding a water-miscible solvent, such as ethanol or acetone at a temperature of −40° to 40° C., preferably −10° to 30° C., and most preferably 0° to 10° C.

For the recrystallization of the pyro-derivative the partially purified precipitate may be resuspended at about 0.001–1 g/ml, more preferably 0.01–0.5 g/l and still more preferably at 0.05-0.15 g/ml. Most preferred is to resuspend the precipitate at about 0.1 g/ml, at a temperature of about 0° to 40° C., more preferably 10°-30° C., and still more preferably at about 15°-25° C. The crystallization of the purified pyro-derivative can be accomplished with an organic solvent, such as ethanol or acetone, at a temperature of about −40° to 40° C., more preferably −10° to 30° C. and still more preferably at about 0° to 10° C. The precipitates may be collected by filtration, preferably in vacuo and lyophilization or drying in vacuo.

The time of heating required for effecting quantitative conversion depends upon the pH, the temperature and the compounds used. For nopaline, at a temperature of 100° C. and a pH of 3.2, quantative conversion was obtained in approximately 2 hours. At a pH of 0.0 and 100° C., conversion was completed in approximately 1.0 hours. At 121° C. the conversion was approximately 30 minutes. At 60° C. conversion was considerably slower, requiring 18-24 hours. At a pH above approximately 5.5, conversion to the pyro-derivatives was too slow to be readily measured in 48 hours at 100° C.

For isonopaline, conversion times were considerably longer under equivalent conditions. For example, the reaction at 60° C., pH 3.2 was completed in approximately 100 hours. The reaction rate constants for nopaline and isonopaline were $4.6 \times 10^{-7} s^{-1}$ and $0.35 \times 10^{-7} s^{-1}$.

A further method of the present invention hereby provided is that for the synthesis of nopalinic acid or a derivative of nopalinic acid (isonopalinic acid or a derivative of isonopalinic acid), comprising:

dissolving in aqueous base a compound of the formula:

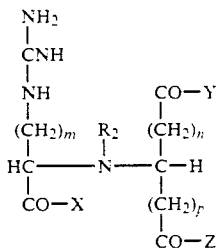

wherein X, Y, Z, $R_1$, $R_2$, m, n and p are as hereinbefore defined, whereby a basic solution of the compound is formed;

heating said basic solution whereby a product-containing crude solution is obtained;

separating said product from the crude solution, thereby obtaining a partially purified solid product;

dissolving the partially purified solid product in water, thereby obtaining an aqueous solution of the partially purified solid product;

adjusting the pH of the aqueous solution containing the partially purified product to the approximate isoelectric point of the compound, whereby a pH-adjusted solution is obtained;

adding to the pH-adjusted solution a water miscible organic solvent having a dielectric constant lower than that of water, until a partially purified precipitate forms; and collecting said partially purified precipitate.

The method of synthesizing nopalinic acid or a nopalinic acid derivative (or isonopalinic acid or a isonopalinic acid derivative), may also comprise the following steps to separate a partially purified solid product from the rest of the basic heated solution:

evaporating the heated solution to dryness whereby a crude solid product is obtained;

dissolving said crude solid product in water to obtain an aqueous solution of the crude solid product;

adjusting the pH of the solution of the crude solid product to a pH of below about 3 whereby a pH-adjusted solution of the crude solid product is obtained;

subjecting the pH-adjusted solution to cationic chromatography thereby obtaining a solution containing a partially purified product; and drying the partially purified product solution to obtain a partially purified solid product.

Some of the preferred conditions for the synthesis of a nopalinic acid derivative or its diastereoisomer are those wherein the starting compound is dissolved at between about 0.01-30% (w/v) in a basic solution of approximately 0.01 to 10M base and heating of the basic solution is carried out at between 40°-200° C. for between about 30 min. to 200 hours.

Other preferred conditions are dissolving the compound at about 0.1 to 20% (w/v) in a basic solution of about 0.05-5M base, heating the basic solution of the compound to about 60°-130° C. for 2-50 hrs. Still further preferred condition are dissolving the compound at about 1-10% (w/v) in a 0.1-2M basic solution, heating the basic solution of the compound at about 80°-120° C. for about 4 to 30 hrs.

Preferred conditions for evaporating the crude solution of a nopaline acid derivative or its diasteroisomer are by lyophilization or drying in vacuo.

Preferred conditions for dissolving the crude and partially purified solid nopalinic acid derivative or its diastereoisomer are 0.01-30% (w/v), preferably 0.1-20% (w/v). Other preferred conditions for dissolving are 1-10% (w/v), preferably 3 to 8% (w/v).

Preferred conditions for adjusting the pH of the solutions of the crude and partially purified nopalinic acid derivative or its diastereoisomer are below about 2 and about 1-9, preferablly below 1 and about 2-7, respectively. Other preferred conditions for adjusting the pH of the partially purified solution are to about 3-3.6.

Cationic chromatography of the pH-adjusted crude solution of the nopalinic acid derivative or its diastereoisomer can be done with a strong cationic substrate, e.g., Dowex-50 (H+ form).

Drying of the partially purified nopalinic acid derivative or its diastereoisomer is preferably done by lyophilization or drying in vacuo.

Compounds which can be prepared by the methods of the present invention include those having the following formula:

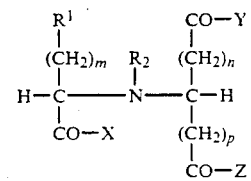

wherein
m is 1-4, n is 0-3, p is 0-3,

X, Y and Z are the same or different and represent is OH or $NH_2$, with the proviso that at least of X, Y and Z is OH.

$R_1$ is $-NHC(NH)NH_2$, $-NH_2$, $-ONH_2$, $-ONH-CONH_2$, $-NH-CO-NH_2$, or $-ONHC(NH)NH_2$, $C_a$ and $C_b$ can be the same or different and represent the R and S carbon configurations, $R_2$ is H and if n or p are different from zero, $R_2$ and Y may be a cyclic structure containing one carbon ring.

Figure 2:
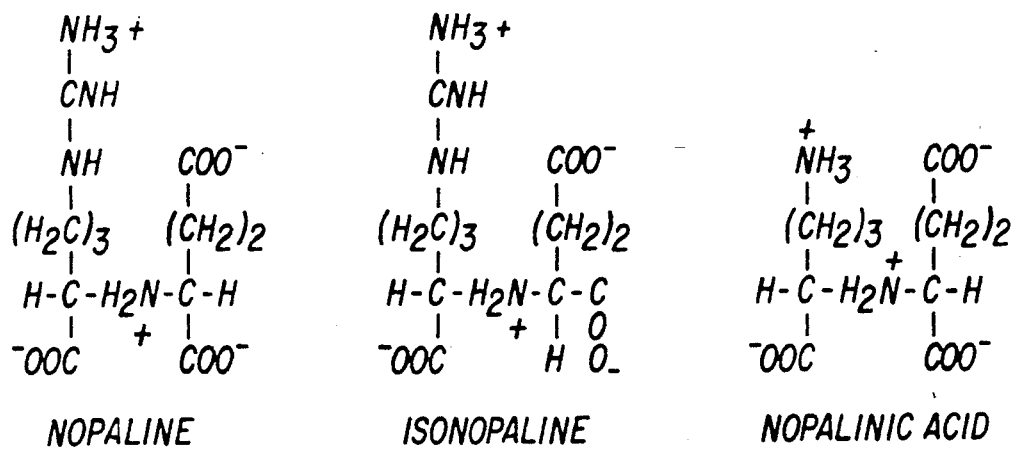
FIG. 2 shows the chemical structure of known nopaline derivatives of the present invention.

Some of these compounds were known in the prior art. The structures of the known compounds are shown in FIG. 2. These compounds are nopaline itself, isonopaline and nopalinic acid. However, these compounds have never previously been obtained with the degree of purity of the present invention.

All the remaining compounds of this invention are novel and have never been described or suggested prior to this invention.

Preferred are compounds in which $R_1$ and Y are a cyclic structure containing one carbon ring, and n or p are greater than zero. These compounds are known as pyronopaline and pyroisonopaline derivatives. Also preferred are amide derivatives of the present compounds wherein X, Y or Z are $-NH_2$.

Also preferred are compounds where $R_1$ is $-O-N-H-CO-NH_2$. These compounds are also known as canavano derivatives. Another group of preferred compounds are those wherein $R_1$ is $-NH-CO-NH_2$.

Preferred are those compounds wherein $R_1$ is $-O-NH_2$, and $C_a$ is in the S carbon configuration and $C_b$ is in the R carbon configuration.

Also preferred are compounds wherein $R_1$ is $-O-NH_2$, and $C_a$ and $C_b$ are in the S carbon configuration.

Also preferred are compounds wherein n is 1. These compounds are known as carboxyoctopine derivatives.

Still another group of preferred compounds are those wherein n is 1 and p is 1. This are the derivatives of the heretofore unknown compound derived from dicarboxyacetone and arginine.

Still another group of preferred compounds are those wherein $R_1$ is $-NH_2$. These are known as derivatives of nopalinic and isopalinic acid.

A further group of preferred compounds are those wherein $R_1$ is $-O-NH-CNH-NH_2$.

Some of the most preferred compounds of this invention are those represented by the general structure shown hereinbefore, and wherein:

$R_1$ is $NH_2$, $R_2$ is H, $m=3$, $n=2$, $p=0$, X, Y and $Z=OH$, and $C_a$ and $C_b$ are in the S carbon configuration, also known as isonopalinic acid;

the compound wherein $R_1=-NH-CNH-NH_2$, $m=3$, $n=2$, $p=0$, X and $Z=OH$, $C_a$ and $C_b$ are in the S carbon configuration, and $R_2$ and Y are a cyclic structure containing a carbon ring also known as pyroisonopaline;

the compound wherein $R_1=-O-NH-CO-NH_2$, $m=3$, $n=2$, $p=0$, X, Y and $Z=OH$ and $C_a$ and $C_b$ are in the S carbon configuration or canavanoisonopaline;

the compound wherein $R_1$ is $-O-NH-CO-NH_2$, $m=3$, $n=2$, $p=0$, X, Y and $Z=OH$, $C_a$ is in the S carbon configuration and $C_b$ is in the R carbon configuration, or canavanonopaline; and the compound wherein $R_1$ is $-NH-CNH-NH_2$, $m=3$, $n=2$, $p=0$, X, Y and $Z=OH$, $C_a$ is in the S carbon configuration, $C_b$ is in the R carbon configuration, and $R_2$ and Y are a cyclic structure containing one carbon ring, or pyronopaline;

the compound wherein $R_1$ is $-NH-CNH-NH_2$, $m=3$, $n=1$, $p=0$, X, Y and $Z=OH$, $C_a$ is in the S carbon configuration and $C_b$ in the R carbon configuration or carboxyoctopine; and the compound wherein $R_1=-NH-CNH-NH_2$, $m=3$, $n=1$, $p=1$, X, Y and $Z=OH$, $C_a$ is in the S carbon configuration and $C_b$ is in the R carbon configuration, which is yet unnamed.

The compounds of the present invention are useful as a C or N source for the bacterium *A. tumefaciens*.

The present invention provides bacterial growth media, comprising the present compounds. The media may contain other nutrients, such as minerals, trace elements, etc. as needed, in addition to the present compounds. A standard method of growing the bacterium is by preparing media comprising a compound of the present invention or a mixture thereof supplemented as needed to support the growth of the bacterium.

This method is useful in selecting the strains of bacterium which can metabolize a compound of the present invention. This strain of bacterium will be capable of growing in the presence of a compound of this invention, while other strains which are not capable of metabolizing the compound will perish.

Since the capability for metabolizing the present compound is conferred to the bacterium by the Ti plasmid, genetically engineered *A. tumefaciens* bacteria having specific Ti plasmid vectors or sequences conferring the capability for metabolizing different compounds, can also be selectively grown by the media comprising the present compounds.

In addition, cells which contain the Ti-plasmid, vectors or sequences derived from the plasmid can be grown in the media of this invention. Cells which are representative are crown gall tumor cells.

The concentration of the present compounds in the growth media can vary over a wide range as is known by those skilled in the art of growing bacteria or plant cells. Generally, a concentration of between about 0.05 and 20 g per l, most preferably a concentration of between about 2 and 5 g per l for most *A. tumefaciens* bacterial strains or plant cells would be sufficient.

Having now generally described this invention, the same will be understood by reference to certain specific examples which are included herein for purposes of illustration only and are not intended to be limiting unless otherwise specified.

EXAMPLES

Example 1: Synthesis of Nopaline and Isonopaline 8.4 grams of arginine and 29.2 grams of α-oxoglutarate were reacted with 9.4 grams of cyanoborohydride in 60 ml of solution at a pH to 7.0 for 48 hours. The reaction mixture was then acidified to pH 0.8 and allowed to release HCN. Then, the mixture of nopaline and isonopaline was applied to a Dowex-50 (H+ form column). The column was washed with 2 volumes of water and eluted with 1M aqueous ammonia to obtain a mixture of the diastereoisomers. After drying in vacuo on a rotary evaporator, the solid material was dissolved in 100 ml of water at a concentration of about 0.1 g/ml. The pH of the solution was adjusted to about 3.2 with 14 ml of 3M HCl and allowed to stand at 4° C. for 24 hours, and nopaline-enriched crystals were then obtained. The crystals were filtered under vacuum and dried. The purity of the obtained nopaline crystals was determined by electrophoresis or HPLC and was found to be approximately 98%. The yield was 6.5 g of nopaline.

For recrystalization, the crystals were suspended in water at room temperature at a concentration of 0.1 g/ml and dissolved by the slow addition of 2M aqueous ammonia to a pH of about 5.0. The pH was then adjusted to 3.2 with HCl and the solution was then chilled at 4° C. for 24 hours as previously described. After chilling, the crystals were harvested by filtration and dried in vacuo at room temperature. The yield was 5.3 g.

Isonopaline was obtained from the mother liquor of the first nopaline crystallization by the addition of 3 volumes of 95% ethanol and chilling at 4° C. for 36 hours. An additional recrystallization was carried out under the following conditions.

At this point the physical properties of the nopaline and isonopaline were constant. Analysis of the compound showed that it was at least 99% pure. Other characteristics of these compounds are shown in Table 1.

TABLE 1:

| | Properties of Isomers and Derivatives of Nopaline | | |
|---|---|---|---|
| COMPOUND | NOPALINE | ISONOPALINE | PYRONOPALINE |
| EMPIRICAL FORMULA | $C_{11}H_{20}N_4O_6 \cdot H_2O$ | $C_{11}H_{20}N_4O_6 \cdot H_2O$ | $C_{11}H_{18}N_4O_5$ |
| Elemental analysis (theor) | | | |
| C % | 40.70 (40.98) | 40.84 (40.98) | 45.96 (46.15) |
| H % | 6.86 (6.88) | 6.91 (6.88) | 6.40 (6.33) |
| N % | 17.26 (17.34) | 17.34 (17.34) | 19.42 (19.57) |
| O % | 35.18 (34.75) | 34.91 (34.75) | 28.22 (27.94) |
| Melting Point (°C., uncorr) | 184 | 160 | 245 (dec) |
| Optical rotation $[\alpha]_D^{22}$, (deg) (c = 0.5, $H_2O$) | $+19 \pm 1$ | $+27 \pm 1$ | $-40 \pm 1$ |
| Solubility in $H_2O$ (mg/ml, 22° C.) | 6.3 | 21.3 | 34.5 |

Infrared spectra were determined on a Perkin-Elmer Model 221 spectophotometer and $^1$H-NMR spectra of samples dissolved in deuterium oxide were determined in the NMR Core Facility of a Bruker WH-400 spctrometer operating at 400 MHz. Chemical shifts are reported in ppm with respect to 3-(trimethylsilyl)-tetradeutero sodium propionate (TSP). Elemental analyses (C, H, and N) were done by Atlantic Microlab, Inc., Atlanta, Ga. Oxygen was determined by difference.

High performance liquid chromatography (HPLC) was done on an LDC-HPLC with an absorbance monitor set at 196 nm connected to a digital integrator. All samples were 0.020 ml. System A consisted of a Regis column (S5 ODS) of Spherisorb, which was developed with $H_3PO_4$ (0.0125M) at 1.0 ml/min. System B consisted of a Whatmann column (10/25 SAX) of Partisil PXS, which was developed with sodium phosphate (0.125M, pH 3.50) at 3.0 ml/min.

Electrophoresis was performed on paper strips (Whatmann 1) in one of the following: sodium carbonate, (0.05M, pH 10.0); potassium phosphate (0.02M, pH 7.0); formic acid:acetic acid:water (5:15:80); or HCl (0.01M). The electric field was 100 v/cm. Guanidinium compounds were identified by fluorescence produced with the phenanthrenequinone reagent described by Otten and Schilperoort, BBA 527:497–500 (1978). The presence of secondary amines was determined by the nitroprusside reaction described by Feigel, in "Spot Tests in Organic Analysis", pp 260–262, Elsevier, N.Y. (1956).

The properties of the nopaline and isonopaline synthesized as described above were consistent with the structures proposed previously. Furthermore, the fact that octopine dehydrogenase from scallops (Pecten maximus) which catalyzes the oxidation of D-octopine but not of L-allooctopine catalyzed the oxidation of nopaline but not that of isonopaline indicates that the absolute configuration of nopaline is designated as:

N-(4-((aminoiminomethyl)amino-)-1S-carboxybutyl)-2R-2-pentanedioic acid. Naturally occurring nopaline isolated from crown gall tumor corresponds to synthetic nopaline by its optical rotation $((\alpha)_D^{22}=19\pm1°)$, melting point (183° C.), HPLC in both systems and IR spectra (Table I).

Isolation of Nopaline from Crown Gall Tumor Tissue

Naturally occurring nopaline was isolated from crown gall tumor tissue (CG1CT-T37) which was grown in Murishige and Skoog minimal medium without phytohormones at 23° C. (about 3 weeks) and harvested by filtration through cheesecloth. The tissue was immediately placed in a plastic bag and frozen between two blocks of dry ice. the frozen tissue was dried in vacuo, and the dried material was extracted by suspension in water (60 ml/g, 4° C.) in a waring blender 2 min. . The suspension was centrifuged (10,000×g, 50 min), and the supernate was applied to a column (0.079 times the volume of the extract, 1:5 diameter to height) of Dowex 1-X8 (HO- form). The column was washed with two volumes of water, and the nopaline (determined by HPLC, system A or B) was eluted with aqueous $NH_4Cl$ (0.1M). The eluate that contained nopaline was applied to a column (0.36 times the volume of sample) of Dowex 50W-X8 (H+ form) at 4° C. The column was washed with one column volume of water, and the nopaline was eluted with aqueous ammonia (1M). The eluate that contained nopaline was taken to dryness and left in vacuo overnight. The residue was dissolved in water (10 ml/g) and the pH was adjusted with HCl (1M). After 15 h at 4° C., a crystalline material was filtered that corresponding to nopaline (at least 98%) by HPLC.

Example 2: Synthesis of of Pyronopaline and Pyroisonopaline 1.0 grams of nopaline (or isonopaline) were suspended in 10 ml of water at a pH of 3.2 and heated at 100° C. until the formation of the pyro-derivative was essentially quantitative, as judged by HPLC.

Pyronopaline (or pyroisonopaline) were readily crystallized by adjusting the pH of the reaction mixture to between about 3.0–3.5, adding 5 vol. of alcohol (or 5 vol of acetone) and chilling to −20° C. for 48 hours. The structure of the pyronopaline is confirmed by the results of the elemental analysis also shown in Table I, which corresponds to the empirical formula of a compound derived from nopaline by the loss of water. Thus, the results from the spectral and elemental analysis indicate a correlation for nopaline and pyronopaline similar to that shown for glutamic acid and its pyrrolidonecarboxylic acid derivative. Therefore, the derivative formed from nopaline was designated N-(4-((aminoiminomethyl)amino)-1S-carboxybutyl)-2-pyrrolidone-5R-carboxylic acid or pyronopaline.

Example 3: Structure of Nopaline, Isonopaline, Pyronopaline and Pyroisonopaline Both pyroisonopaline and pyronopaline reacted with the phenanthrenequinone reagent to give a fluorescent compound compound which indicates that the guanidino group remains intact. However, the nitroprusside test for secondary amines was negative with both pyro-derivatives, whereas the test was positive with both nopaline and isonopaline (although only weakly so in the case of the latter compound). In addition comparison of the titration curves of the parent compounds with those of their derivatives showed that the appearance of the latter was associated with the disappearance of a group with a p$K_a$ of 9.2 (presumably the amine). The loss of the amine was further demonstrated by the results of electrophoresis where pyronopaline moved more slowly toward the anode than nopaline at pH 2, whereas they moved at equal rates toward the cathode at neutral pH. The loss of a carboxyl group is indicated by the fact that pyronopaline also moved more slowly than nopaline toward the cathode upon paper electrophoresis at pH 10.0.

FIG. 1 shows the $^1$H-MNR spectra of nopaline (A), pyronopaline (B), and of isonopaline (C). Because of their chemical shifts, their relative sizes, and their splitting: the two peaks at 3.65 and 3.75 ppm in the nopaline spectrum are attributed to the hydrogens on the α-carbons of the glutamate and arginine portions of nopaline. These peaks become overlapping in isonopaline, and in the compound derived from nopaline they shift to 4.15 ppm and overlap even more. The fact that the chemical shift of the analogous hydrogen in reference spectra of glutamate moves from 3.7 to 4.16 upon the formation of the corresponding pyrrolidonecarboxylic acid (Duffy et al, Bioorg. Chem. 5:351–366 (1976)) strongly supports the contention that the nopaline derivative is a similar compound.

The peak at 3.2 ppm in all three spectra is attributed to the hydrogens on the δ-carbon of the arginine portion, and the peaks between 1.6 and 2.0 ppm are attributed to the other methylene carbons of arginine by comparison with spectra of arginine and octopine. The peak at 2.5 ppm in the nopaline spectrum is attributed to the hydrogens on the γ-carbon of the glutamate portion, and as expected, it becomes much more complex in the derivative. The peak at 2.1 ppm is attributed to the hydrogens on the β-carbon of the glutamate portion, and the additional peak at 1.6 ppm in the spectrum of the derivative must be due to one of the same two hydrogens, which become nonequivalent in the pyrrolidonecarboxylic acid ring. The peak at 0.1 ppm is due to an impurity consistently seen in the deuterium oxide.

In addition, further spectroscopic evidence for the proposed structure comes from the fact that pyronopaline has a shoulder in the UV-spectrum at 205 nm, attributed to the lactam, in addition to the peak at 196 nm that is characteristic of the guanidino groups of nopaline, isonopaline, and arginine.

The structure of pyronopaline is finally confirmed by the results of elemental analysis (Table I), which correspond to the empirical formula of a compound derived from nopaline by the loss of water. Since the pyrrolidonecarboxylic acid apparently crystallizes without the mole of water of crystallization that is characteristic of nopaline and isonopaline (*Cooper and Firmin*, and *Hatanaka et al*, both already cited hereinbefore), there is a difference of two moles of water in their respective empirical formulas, one of crystallization and one of formation of the internal amide.

The Stability and Rate of Formation of Pyronopaline

The conversion of both nopaline and its diastereoisomer to the respective pyrrolidonecarboxylic acid derivatives goes to completion in 30 min at pH 3.2 and 120° C. (autoclave), whereas the cyclization of neither nopaline nor isonopaline is demonstrable above pH 5.5. No significant reverse reaction of the nopaline derivative is seen at 100° C. in NaOH, $Na_2CO_3$ (both at 0.1M), or HCl (3M), a condition known to promote the conversion of the pyrrolidonecarboxylic acid derivative of glutamate to glutamic acid (*Wilson and Cannan*, J. Biol. Chem. 119:309–311 (1937). Since nopaline cyclizes rapidly under the latter conditions, the lack of significant reverse reaction is due to the equilibrium and not to the rate of the reaction. Both nopaline and isonopaline react at pH 3.2 and 60° C. to form their respective pyrrolidonecarboxylic acid derivatives in a first order reaction with rate constants of $4.6 \times 10^{-7} S^{-1}$ and $0.35 \times 10^{-7} S^{-1}$, respectively. The faster reaction of the natural isomer, nopaline, is also apparent at 22° C. and 100/° C.

Occurrence and Metabolism of Pyronopaline

Analysis of extracts of crown gall tumors by HPLC (in both solvent systems) demonstrated that the concentration of the pyrrolidonecarboxylic acid derivative of nopaline, identified by retention time and analysis of samples mixed with authentic compounds, in the tumor is 52 μg/g. In addition, the fact that the concentration of both nopaline and pyronopaline in bacteria-free tumor extract (pH 5.3) did not change for 10 days at room temperature, indicates that the derivative was indeed present in the tumor and is not an artifact of extraction or isolation.

Example 4: Growth of *A. tumefaciens*

The minimal medium for bacterial growth was the mineral salt mixture described by *Petit and Tempe*, hereinbefore cited to which glucose was aded to make the final concentration 0.005 g/ml. The control medium was the mineral salt mixture from which the ammonium sulfate was omitted. In order to test whether they would support bacterial growth either nopaline, isonopaline, or the pyrrolidonecarboxylic acid derivative of nopaline or pyronopaline were added separately to the control medium to make the final concentration 0.0045 g/ml.

A single colony from a plate on minimal medium was adapted to liquid medium that contained nopaline. When visibly turbid, the nopaline liquid culture was innoculated (1% innoculum) into minimal liquid medium and into nopaline liquid medium. When turbid, these two cultures were used as inoculum to test the nopaline, isonopaline and pyronopaline in liquid culture media (20 ml in 125 ml flasks). After innoculation (1%), cultures were agitated on a rotary shaker at 1 cycle per second, and growth was monitored by measurement of the turbidity in a spectrophotometer. The turbidity ($A_{650}$) readings were plotted on log paper and the doubling time was determined from the logarithmic portion of the growth curve (Table II).

TABLE II:

Growth of *A. tumefaciens* on Isomers and Derivatives of Nopaline

| Medium | Doubling Time | |
|---|---|---|
| | Preinduced Innoculum hours | Uninduced Innoculum hours |
| Control Medium | no growth | no growth |
| Minimal Medium | 3.9 | 4.0 |
| Control Medium plus Nopaline | 2.8 | 2.8 |
| Control Medium plus Isonopaline | no growth | no growth |
| Control Medium plus Pyronopaline | 3.1 | 3.1 |

Table II contains the results of experiments to test the ability of *A. tumefaciens* (strain C-58) to utilize the isomers and derivatives of nopaline as a source of carbon and nitrogen. Both nopaline and its pyrrolidonecarboxylic acid derivatives are metabolized, whereas isonopaline is completely ineffective. The results are the same for both preinduced and uninduced bacteria. As expected the doubling time in minimal medium is greater than that in either nopaline or pyronopaline, since metabolism by the organism is more complex in the former medium. However, the fact that the doubling time in pyronopaline is longer than that in nopaline suggests that one or more additional processes are required for growth on the derivative as well.

Example 5: Synthesis of Nopalinic Acid 2 grams of nopaline were dissolved in 35 ml of 1M NaOH and the solution was heated at 100° C. for 12 hours. The reaction mixture was evaporated to dryness to remove ammonia and the crude solid material was dissolved in 25 ml of water. The pH was adjusted to 0.8 to 1.0 and the pH-adjusted solution was chromatographed on a strong cationic exchange column ($H^+$ form). After washing with two column volumes of water, the column was eluted with 10% aqueous ammonia. The eluate containing the nopalinic acid was evaporated to dryness, dissolved in 15 ml of water, adjusted to pH 3.2-3.5 with 1M HCl, and recrystallized by adding approximately 1.5 volumes of ethanol (or acetone). The crystals were recrystallized from aqueous acetone. The characteristics of the compound were as follows:

Yield: 0.89 g (44%).
Melting point: 189°-190° C.
Optical Rotation $(\alpha)_D^{26}$: +15.25.
$^1$H-MNR: 1.75, 2.00, 2.50, 2.90 and 3.75 ppm.
Analysis: $C_{10}H_{17}O_6N_2$.
Theoretical: C 46.02, H 6.51, N 10.75, O 36.8.
Found: C 45.66, H 6.90, N 10.75, O 37.0.

Example 6: Synthesis of Pyronopalinic Acid from Pyronopaline 2.0 grams of pyronopaline were dissolved in 35 ml of 1M NaOH and heated at 100° C. for 15 hours. The reaction mixture was treated as described for the synthesis for nopalinic acid in Example 5. The product was crystallized from aqueous acetone. The characteristics of the product were as follows:

Yield: 1.1 g (55%).
Melting Point: 148°-150° C.
$^1$H-NMR: 1.75, 2.00, 2.50, 2.90, and 3.75 ppm.

Example 7: Synthesis of Pyronopalinic Acid from Nopalinic Acid 0.5 g of nopalinic acid was dissolved in water a concentration of 0.1 g/ml and a pH of about 3.2. The solution was heated at 100° C. to cause cyclization to the pyrrolidonecarboxylic acid derivative. The product was isolated by crystallization from aqueous acetone. The characteristics of the compound were as follows:

Yield: 0.22 g (44%).
Melting Point: 148°-150° C. .
$^1$H-NMR: 1.75, 2.00, 2.50, 2.90 and 3.75 ppm.

Example 8: Synthesis of Canavanonopaline and Canavanoisonopaline 1.0 g of canavanine and 3.5 g of 2-oxoglutarate were dissolved in water (6.0 ml, pH 8.0) at room temperature. 0.9 g of sodium cyanoborohydride were added and the solution was left at room temperature for 24 hrs. The reaction mixture was acidified to pH 0.8 and allowed to release HCN. Then the mixture was applied to a column (30 ml total volume) of Dowex-50 $H^+$ form), and the column was washed with 2 volumes of water. The column was developed with aqueous ammonia (1M) and the eluate was dried in vacuo. Canavanonopaline was crystallized by lowering the pH to the isoelectric point (pH 3.2) and adding a small amount of ethanol. Canavanoisonopaline was crystallized from the mother liquor by the addition of more ethanol. The properties of both compounds are listed below.

| | Canavanonopaline | Canavanoisonopaline |
|---|---|---|
| Yield | 170 mg | 150 |
| M.P. | 182° C. | 180° C. |
| NMR | 2.15, 2.3, 2.45, 2.5, 3.6, 3.9, 4.1 | 2.0, 2.15, 2.4, 3.05, 3.3, 3.5 |
| KMNO$_4$ Oxidation | yields no L-glutamate | yields L-glutamate |
| Elemental analysis | | |
| C | 37.81 (36.95) | 36.40 (36.95) |
| H | 6.09 (6.22) | 6.22 (6.22) |
| N | 18.28 (17.28) | 18.24 (17.28) |
| O | 37.82 (39.46) | 39.14 (39.46) |

Having now fully described this invention, it will be appreciated by those of skill in the art that the same can be practiced within a wide and equivalent range of compositions. mode of use, and the like, without affecting the spirit or scope of the invention or any embodiment thereof.

What is claimed as new and intended to be covered by Letters Patent of the United States is:

1. A method of separating nopaline from its diastereoisomer in a mixture containing nopaline and the diastereoisomer thereof, which consists essentially of:
   a) dissolving the mixture in water to form an aqueous solution of nopaline and the diastereoisomer thereof,
   b) adjusting the pH of the aqueous solution to within a pH range of from 1 to 9,
   c) precipitating nopaline from the aqueous solution, and
   d) collecting nopaline which is at least 98% pure, and at least 98% free of its diastereoisomer.

2. The method of claim 1, which further comprises subjecting the collected substantially pure precipitate to steps a) through d).

3. The method of claim 1, wherein said pH of said mixture is adjusted to between 3.0 to 3.6.

4. The method of claim 1, wherein said mixture is dissolved in water at a concentration of about 0.05 to 0.15 g/ml.

5. The method of claim 1, wherein the dissolution of the mixture of nopaline and its diastereoisomer in water is effected at a temperature of from about 0° to 40° C.

* * * * *